(12) United States Patent
Andersen

(10) Patent No.: US 12,138,435 B2
(45) Date of Patent: Nov. 12, 2024

(54) INFUSION FLUID WARMER COMPRISING PRINTED CIRCUIT BOARD HEATING ELEMENTS

(71) Applicant: Mequ A/S, København N (DK)

(72) Inventor: Ulrik Krogh Andersen, Hellerup (DK)

(73) Assignee: MEQU A/S, Copenhagen (DK)

( * ) Notice: Subject to any disclaimer, the term of this patent is extended or adjusted under 35 U.S.C. 154(b) by 477 days.

(21) Appl. No.: 17/379,911

(22) Filed: Jul. 19, 2021

(65) Prior Publication Data

US 2021/0338945 A1 Nov. 4, 2021

Related U.S. Application Data

(63) Continuation of application No. 17/118,655, filed on Dec. 11, 2020, which is a continuation of application
(Continued)

(30) Foreign Application Priority Data

Aug. 14, 2015 (EP) .................................... 15181113

(51) Int. Cl.
*A61M 5/44* (2006.01)
*A61M 5/14* (2006.01)
(Continued)

(52) U.S. Cl.
CPC ................ *A61M 5/44* (2013.01); *A61M 5/14* (2013.01); *H05B 1/0227* (2013.01);
(Continued)

(58) Field of Classification Search
CPC .. A61M 2205/3368; A61M 2205/3653; A61M 2205/8206; A61M 5/14;
(Continued)

(56) References Cited

U.S. PATENT DOCUMENTS 3,789,190 A * 1/1974 Orosy ................ G05D 23/2401
219/494
4,293,762 A 10/1981 Ogawa
(Continued)

FOREIGN PATENT DOCUMENTS

| CN | 2385736 A | 7/2000 |
|---|---|---|
| CN | 2756247 Y | 2/2006 |

(Continued)

OTHER PUBLICATIONS

International Search Report in corresponding International Application No. PCT/EP2016/067077, mailed Sep. 30, 2016 (3 pages).
(Continued)

*Primary Examiner* — Sang Y Paik
(74) *Attorney, Agent, or Firm* — Ice Miller LLP

(57) ABSTRACT

The present invention relates to an infusion fluid warmer comprising a heat exchanger and first and second printed circuit boards comprising respective integrally formed electrically resistive patterns acting as heating elements. The integrally formed electrically resistive patterns are heated by supply of electrical power and thermally coupled to a heat exchanger to warm an infusion fluid flowing through a fluid passage of the heat exchanger.

17 Claims, 9 Drawing Sheets

Related U.S. Application Data

No. 15/752,316, filed as application No. PCT/EP2016/067077 on Jul. 18, 2016, now Pat. No. 10,888,671.

(51) Int. Cl.
   *H05B 1/02* (2006.01)
   *H05B 3/22* (2006.01)

(52) U.S. Cl.
   CPC ............ *H05B 1/0244* (2013.01); *H05B 3/22* (2013.01); *A61M 2205/3368* (2013.01); *A61M 2205/3653* (2013.01); *A61M 2205/8206* (2013.01); *H05B 2203/021* (2013.01)

(58) Field of Classification Search
   CPC ..... A61M 5/44; H05B 1/0227; H05B 1/0244; H05B 2203/021; H05B 3/22
   See application file for complete search history.

(56) References Cited

U.S. PATENT DOCUMENTS

| | | | |
|---|---|---|---|
| 4,478,076 | A | 10/1984 | Bohrer |
| 4,574,876 | A | 3/1986 | Aid |
| 4,680,445 | A | 7/1987 | Ogawa |
| 4,735,609 | A | 4/1988 | Comeau |
| 5,245,693 | A | 9/1993 | Ford |
| 5,381,510 | A | 1/1995 | Ford |
| 5,690,614 | A | 11/1997 | Carr |
| 5,822,993 | A * | 10/1998 | Attey ............... H10N 10/13 62/3.2 |
| 6,036,654 | A | 3/2000 | Quinn |
| 6,146,359 | A | 11/2000 | Carr |
| 6,146,395 | A | 11/2000 | Kanz |
| 6,175,688 | B1 | 1/2001 | Cassidy |
| 6,317,248 | B1 | 11/2001 | Agrawal |
| 6,336,003 | B1 | 1/2002 | Mitsunaga et al. |
| 6,641,556 | B1 | 11/2003 | Shigezawa |
| 6,666,907 | B1 | 12/2003 | Manginell |
| 6,788,885 | B2 | 9/2004 | Mitsunaga |
| 7,132,627 | B2 | 11/2006 | Peyronny |
| 7,167,776 | B2 | 1/2007 | Maharajh |
| 7,731,688 | B2 | 6/2010 | Park |
| 7,865,072 | B2 | 1/2011 | Cassidy |
| 8,467,671 | B2 | 6/2013 | French et al. |
| 8,554,064 | B1 * | 10/2013 | Dinh ............... A61M 16/18 392/397 |
| 8,948,581 | B2 | 2/2015 | French et al. |
| 9,211,381 | B2 | 12/2015 | Faries |
| 9,717,862 | B2 | 8/2017 | Anderson |
| 10,588,350 | B2 | 3/2020 | Yu |
| 10,888,671 | B2 * | 1/2021 | Andersen ............... A61M 5/44 |
| 2002/0081109 | A1 | 6/2002 | Mitsunaga |
| 2002/0181948 | A1 | 12/2002 | Akahane |
| 2003/0135250 | A1 | 7/2003 | Lauman |
| 2005/0008354 | A1 | 1/2005 | Cassidy |
| 2007/0137646 | A1 | 6/2007 | Weinstein |
| 2008/0077087 | A1 | 3/2008 | Martens |
| 2008/0156476 | A1 * | 7/2008 | Smisson ............... A61M 5/36 219/541 |
| 2010/0222740 | A1 | 9/2010 | Park |
| 2011/0022115 | A1 | 1/2011 | Salzhauer et al. |
| 2011/0034866 | A1 | 2/2011 | Zhang et al. |
| 2011/0054453 | A1 | 3/2011 | Lalonde et al. |
| 2011/0152767 | A1 | 6/2011 | Pinedjian et al. |
| 2011/0169343 | A1 | 7/2011 | Cassidy |
| 2011/0194846 | A1 | 8/2011 | Wang et al. |
| 2011/0198343 | A1 | 8/2011 | Bilchinsky et al. |
| 2011/0202034 | A1 | 8/2011 | Lopez |
| 2011/0229615 | A1 | 9/2011 | Pedersen |
| 2014/0072288 | A1 | 3/2014 | Newell |
| 2014/0276545 | A1 | 9/2014 | Andersen |
| 2015/0290844 | A1 * | 10/2015 | Ikawa ............... B29C 33/3842 205/221 |
| 2015/0359263 | A1 | 12/2015 | Bellinger |
| 2017/0367410 | A1 * | 12/2017 | Hon ............... H05B 1/0297 |

FOREIGN PATENT DOCUMENTS

| | | |
|---|---|---|
| CN | 101374563 A | 2/2009 |
| CN | 101612425 A | 12/2009 |
| CN | 101947339 A | 1/2011 |
| CN | 201692416 U | 1/2011 |
| CN | 201692430 U | 1/2011 |
| CN | 201692444 U | 1/2011 |
| CN | 201692445 U | 1/2011 |
| CN | 201692448 U | 1/2011 |
| CN | 201701577 U | 1/2011 |
| CN | 201701585 U | 1/2011 |
| CN | 201701586 U | 1/2011 |
| CN | 201710765 U | 1/2011 |
| CN | 201710766 U | 1/2011 |
| CN | 201719650 U | 1/2011 |
| CN | 201727734 U | 2/2011 |
| CN | 201727808 U | 2/2011 |
| CN | 201727809 U | 2/2011 |
| CN | 201735015 U | 2/2011 |
| CN | 201744029 U | 2/2011 |
| CN | 201755349 U | 3/2011 |
| CN | 201759946 U | 3/2011 |
| CN | 201768233 U | 3/2011 |
| CN | 201768234 U | 3/2011 |
| CN | 201783036 U | 4/2011 |
| CN | 201791194 U | 4/2011 |
| CN | 201798977 U | 4/2011 |
| CN | 102058919 A | 5/2011 |
| CN | 201814947 U | 5/2011 |
| CN | 201832201 U | 5/2011 |
| CN | 102105188 A | 6/2011 |
| CN | 201862059 U | 6/2011 |
| CN | 201862080 U | 6/2011 |
| CN | 201888972 U | 7/2011 |
| CN | 201888973 U | 7/2011 |
| CN | 104010682 A | 8/2014 |
| EP | 1066844 A1 | 1/2001 |
| EP | 2311514 A2 | 4/2011 |
| EP | 2366419 A1 | 9/2011 |
| JP | 06-114003 A | 4/1994 |
| JP | 09-500481 A | 1/1997 |
| JP | 2004524056 A | 8/2004 |
| JP | 2007-527495 A | 9/2004 |
| JP | 2007-516007 A | 6/2007 |
| JP | 2011024626 A | 2/2011 |
| JP | 2011528930 A | 12/2011 |
| JP | 2014-528811 A | 10/2014 |
| RU | 2009133512 A | 3/2011 |
| WO | 9503680 | 2/1995 |
| WO | 9709076 A1 | 3/1997 |
| WO | WO 99/026690 A1 | 6/1999 |
| WO | 0162194 A1 | 8/2001 |
| WO | 03049790 A1 | 6/2003 |
| WO | 2005009500 | 2/2005 |
| WO | WO 2005/027578 A | 3/2005 |
| WO | 2011015912 A1 | 2/2011 |
| WO | 2011015961 A1 | 2/2011 |
| WO | 2011035238 A2 | 3/2011 |
| WO | 2011045011 A1 | 4/2011 |
| WO | 2011097487 A2 | 8/2011 |
| WO | 2011113421 A2 | 9/2011 |
| WO | 2012155149 A1 | 11/2012 |
| WO | WO 2012/155149 A2 | 11/2012 |
| WO | WO 2013/053674 A1 | 4/2013 |

OTHER PUBLICATIONS

Written Opinion in corresponding International Application No. PCT/EP2016/067077, mailed Sep. 30, 2016 (6 pages).

* cited by examiner

INFUSION FLUID WARMER COMPRISING PRINTED CIRCUIT BOARD HEATING ELEMENTS

CROSS-REFERENCE TO RELATED APPLICATIONS

This application is a continuation of pending U.S. patent application Ser. No. 17/118,655, filed Dec. 11, 2020, which is a continuation of U.S. patent application Ser. No. 15/752,316, filed, Feb. 13, 2018, now U.S. Pat. No. 10,888,671, which is a U.S. National Stage of International Application No. PCT/EP2016/067077, filed Jul. 18, 2016, which claims the benefit of European Patent Application No. 15181113.0, filed Aug. 14, 2015, all of which are incorporated herein by reference in their entireties.

The present invention relates to an infusion fluid warmer comprising a heat exchanger and first and second printed circuit boards comprising respective integrally formed electrically resistive patterns acting as heating elements. The integrally formed electrically resistive patterns are heated by supply of electrical power and thermally coupled to a heat exchanger to warm an infusion fluid flowing through a fluid passage of the heat exchanger.

BACKGROUND OF THE INVENTION

Intravenous, intraosseous or infusion fluids such as blood are commonly used in hospitals. Infusion fluids are also used in the field for example during patient transportation in disaster areas or war zones from an accident site to a hospital. The patient may be transported in a vehicle such as an ambulance or helicopter. The infusion fluid is used during most medical procedures and applications. Such infusion fluid is typically delivered from an IV fluid bag or container into a blood vessel of a patient. Blood is refrigerated during storage while other types of infusion fluids may be kept at ambient temperatures.

It would potentially be life threatening for the patient and may lead to hypothermia if the infusion fluid is infused into the patient's body directly from storage at storage temperatures. Therefore, it is necessary to warm the infusion fluid to a temperature close to a desired body temperature of the patient to avoid administration of under-heated infusion fluid causes a drop in the patient's body temperature.

An infusion fluid warmer may be discarded after use or sterilized before the next use. In both cases it is desirable to reduce cost of the fluid warmers as much as possible in order to spend resources economically for the benefit of the patients.

Moreover, portability, reliability, safety-of-use and ruggedness of the infusion fluid warmer is of particular importance for field use where ambulance crews, doctors, paramedics, combat medics or rescue workers need to bring the infusion fluid warmer to hard-to-reach emergency sites or a combat zone. Under these conditions the rescue workers must often provide life-saving first aid to injured persons, possibly in crammed spaces and dangerous conditions due to for example danger of collapsing building structures or enemy fire. Therefore, it is of particular importance that the size, weight and parts count of the infusion fluid warmer is reduced as much as possible. The power supply for the infusion fluid warmer, e.g. comprising rechargeable batteries, must also be transported to the rescue site. Therefore, a high energy efficiency of the infusion fluid warmer is advantageous to limit the size and weight of the power supply.

WO 2005/027578 discloses an infusion fluid warmer with a PCB-type heater. The embodiment disclosed in example 3 and FIG. 9 comprises a body with a support for an inlet connection. The inlet connection is in communication with a flow path defined by a plurality of walls protruding from the body and forming a zigzag pattern. The flow path is closed by a cover that is adhered to the walls for preventing the fluid from flowing out. The flow path terminates in an outlet connection.

WO 2005/027578 discloses two PCB-type heaters that are inserted into at least one inside of the inside of the body and the inside of the cover, respectively. The body is made of ABC and the cover is made of PE. The PCB-type heater is established by a heating resistor formed by a circuit pattern on an insulating substrate. An insulating film of an undisclosed material is placed over the heating resistor for protection. As best understood the PCB-type heater on the inside of the inside of the body is embedded in the ABC material. Therefore the heater must heat through the ABC material and the insulating film. This also applies to the heater on the inside of the cover that must heat through the PE and insulating film.

It is a disadvantage of the infusion fluid warmer in WO 2005/027578 that the heating is applied through the ABC and PE material as polymers generally have a low thermal conductivity. The heating is therefore slowly reacting and not very efficient.

The infusion fluid warmer is controlled based on a temperature reading from a temperature sensor located on the insulating substrate. The temperature sensor measures the temperature of the heater and indirectly measures the temperature of the infusion fluid in the flow path through the ABC and insulating film and PE and insulating film respectively. WO 2005/027578 discloses multiple solutions for establishing said temperature sensor for measuring the temperature of the heater, one of which is illustrated in FIG. 5.

The heating resistor is formed by coating the one side of the insulating substrate with different materials forming two resistors having a large thermoelectric power in order to heat when power is applied or form a thermocouple as power is removed. The two resistors are coupled by a via hole. The thermocouple will measure the temperature of the heater at the junction when power is removed.

The fluid should not have the same temperature as the measured temperature of the heater at the junction as the fluid is separated from the junction by the ABC or PE material and insulating film.

In view of the above-mentioned shortcomings of prior art devices, it is one object of the invention to provide an infusion fluid warmer with more accurate control of the fluid temperature than the prior art devices.

A further object of the present invention is to provide an energy efficient, compact, reliable and cost-effective infusion fluid warmer.

SUMMARY OF THE INVENTION

A first aspect of the invention relates to an infusion fluid warmer comprising:
  a DC power supply input,
  a first printed circuit board comprising a first surface and
    a second, opposing, surface, wherein the second surface comprises a first integrally formed electrically resistive pattern, a second printed circuit board comprising a first surface and a second, opposing, surface, wherein the second surface comprises a second integrally formed electrically resistive pattern, a heat exchanger comprising an upper wall structure and a lower, opposing, wall structure separated by a fluid channel or passage extending between fluid inlets and outlets of the heat exchanger; and a controller for connecting the DC power supply input to the first and/or second integrally formed electrically resistive patterns, characterized in that, an outer surface of the upper wall structure is thermally connected to the first resistive pattern and an outer surface of the lower wall structure is thermally connected to the second resistive pattern, and that the controller is configured to:

selectively connecting the DC power supply input to the first and/or second integrally formed electrically resistive patterns during a first time period to dissipate power in the first and/or second integrally formed electrically resistive patterns, determining, during a second time period, a resistance of the first integrally formed electrically resistive pattern and/or a resistance of the second integrally formed electrically resistive pattern, and determining a temperature of the first or second integrally formed electrically resistive pattern based on the determined resistance.

The infusion fluid warmer herewith achieved provides a more responsive and accurate temperature control of the infusion fluid.

By measuring the temperature based on the resistance of the first or second resistive pattern that is in thermal contact with the upper or lower wall structure, respectively, that in turn is in thermal contact with the infusion fluid flowing through the fluid channel or passage, the temperature measurement or determination represents an average temperature across an entire area of the first and/or second integrally formed electrically resistive patterns. The temperature determination is not based on the fluid temperature at a single point along the fluid channel.

In one embodiment of the infusion fluid warmer, the DC power input is provided by a battery or battery pack which may comprise one or more rechargeable battery cells for example Li-ion based battery cells. The battery is configured for providing a specified voltage acceptable by the controller in the infusion fluid warmer.

The DC power supply input is selectively connected to the first and/or second integrally formed electrically resistive pattern(s) based on the need for dissipating power therein. The need for power dissipation being dependent on factors like a flow rate of the infusion fluid through the fluid channel, the infusion fluid temperature at the fluid inlet, the ambient temperature etc.

In some first time periods there will be a need to connect the DC power supply input throughout the period to dissipate enough power in the first and/or second integrally formed electrically resistive patterns. In other first time periods the DC power supply input will be connected during part of the period and disconnected during the remaining period if the necessary power can be dissipated in the first and/or second integrally formed electrically resistive patterns by such operation. In yet other time periods the DC power supply input may be disconnected during the entire first time period if there is no need to dissipate power in the first and/or second integrally formed electrically resistive patterns.

In one embodiment of the infusion fluid warmer, the DC power supply input is provided by a power supply connected to an AC power supply, for example a mains connection. The AC mains voltage is rectified and converted to the required DC voltage for example in an AC-DC converter of the infusion fluid warmer.

The infusion fluid warmer may comprise an outer casing or housing enclosing and protecting some or all of the previously discussed components of the fluid warmer such as the first and second printed circuit boards, heat exchanger etc. The shape, dimensions and other characteristics of the outer casing or housing is discussed in additional detail below with reference to the appended drawings.

Each of the first and second printed circuit boards may be ordinary single-layer of multilayer rigid circuit boards to keep manufacturing costs low. Each of the first and second printed circuit boards comprises an insulating substrate and an electrically conducting pattern. The electrically conductive pattern may establish electrical connections between different electrical components mounted on the first or second printed circuit board. Moreover, the electrically conductive pattern in itself forms a component of the infusion fluid warmer, namely one of the first or second integrally formed electrically resistive patterns. Hence, the first and/or second integrally formed electrically resistive patterns serve(s) as a heater or heating element when power is supplied to the pattern and a temperature sensor in connection with the resistance determination during the second time period. The skilled person will understand that the multi-functionality of the first and/or second integrally formed electrically resistive patterns, or in short first and second resistive patterns, provide a fluid warmer with a small number of separate components, improved reliability and lower costs.

In an embodiment a resistance of each of the first and second integrally formed electrically resistive patterns is less than 11 Ω such as between 1 and 7Ω.

The thermal connection between the first resistive pattern and the outer surface of the upper wall structure of the heat exchanger is established by placing the second surface of the first printed circuit board in direct contact with the outer surface of the upper wall structure. A thermally conductive paste or film may be added to the mating surface, e.g. before assembly, to increase thermal conductivity between the upper wall structure and the first integrally formed electrically resistive pattern.

Similarly, the thermal connection between the second integrally formed electrically resistive pattern and the outer surface of the lower wall structure of the heat exchanger is established by placing the second surface of the first printed circuit board in direct contact with the outer surface of the lower wall structure. A thermally conductive paste or film may be added to the mating surface before assembly to increase the thermal conduction between the lower wall structure and the second resistive pattern. The thermally conductive paste or film may be electrically insulating in both cases.

The upper wall structure and the lower wall structure of the heat exchanger are placed together in a leak-tight relationship. A cavity confined by the upper wall structure and the lower wall structure defines the fluid channel or fluid passage that extends between the fluid inlet and fluid outlet.

In an embodiment of the infusion fluid warmer the fluid channel or passage extends substantially straight in the longitudinal axis of the heat exchanger between the fluid inlet and fluid outlet.

The amount of power that can be dissipated in the first and second resistive patterns and thereby delivered to the infusion fluid in the fluid channel or passage is proportional with the area of the resistive pattern in thermal contact with the upper and lower wall structures, respectively, of the heat exchanger.

When the DC power supply is coupled to the first and/or second resistive patterns during the first time period, the temperature of the surfaces of the upper and lower wall structures, which are in thermal contact with the infusion fluid in the fluid channel, will increase to exceed the temperature of the infusion fluid thereby heating the infusion fluid.

The resistance of the first and/or second resistive pattern is determined or measured during the second time period. The resistance can be measured by introducing a reference resistor in series with the first and second resistive patterns, respectively, when the measurement is carried out. The DC power supply input is connected. The voltage is measured at a reference point between the reference resistor and the first or second resistive pattern, respectively.

Moreover, the voltage of the power supply is measured, or known a priori via its design. As the resistance of the reference resistor is known the resistance of the first or second resistive pattern can be established using Ohm's law and Kirchhoff's circuit laws.

A short second time period is desirable, to limit the power being dissipated in the first or second resistive pattern during the measurement as this may cause power to be dissipated in the first or second resistive pattern.

Alternatively the resistance of the first or second resistive pattern can be measured directly on the terminals to the resistive pattern in question with the DC power supply interrupted or disconnected.

The value of the determined temperature does not have to be an exact temperature reading if the infusion fluid warmer is calibrated by exposing it to a known temperature close to the set temperature of the infusion fluid warmer. Then any manufacturing tolerances will be cancelled or insignificant in relation to the control of the infusion fluid warmer, as the operating range of the temperature of the infusion fluid at the fluid outlet preferably varies in a narrow interval between 36° C. to 42° C. e.g. around a set point or target temperature such as about 39° C.

In an embodiment the DC power supply input is operated as follows:
1. If the determined temperature during the second time period is below a pre-set threshold, a first time period where the DC power supply input is connected to the first and/or second resistive pattern during part of or the complete first time period is initiated.
2. If the determined temperature is above the threshold, a first time period, where the DC power supply input is disconnected during the first time period, may be initiated.

Step 2 may be repeated until the temperature is below the threshold.

The step of connecting the DC power supply input to the first and/or second integrally formed electrically resistive patterns and the step of determining the resistance may be performed separately, such that heating of the infusion fluids with one resistive pattern does not affect the temperature determination of the other resistive pattern.

Alternatively, the first integrally formed electrically resistive pattern may be connected to the DC power supply input, while at the same time the resistance for the second integrally formed electrically resistive pattern is determined and vice versa. In other words the first integrally formed electrically resistive pattern may be in a first time period, while at the same time the second integrally formed electrically resistive pattern is in a second time period and vice versa.

The reliability of the above-described infusion fluid warmer construction is high because the parts count is reduced as the same components are used for multiple purposes as discussed previously. The first and second resistive patterns are preferably made of one material only. Therefore the manufacturing is cost-effective and any disadvantages in relation to the reliability of arranging and operating dissimilar materials on the same printed circuit board are eliminated.

In a further embodiment, the infusion fluid warmer according to the invention comprises an electronic switching circuit comprising a first switch state and a second switch state selectable in accordance with a control signal of the controller. The electronic switching circuit is configured for connecting the DC power supply input to the first or second integrally formed electrically resistive patterns by selection of the first switch state and configured for disconnecting the DC power supply input to the first or second integrally formed electrically resistive patterns by selection of the second switch state.

In a further embodiment of the present infusion fluid warmer the controller is configured for providing a predetermined delay time, such as between 10 ms and 200 ms, when switching from the first time period to the second time period. The DC power supply to the first or second integrally formed electrically resistive pattern is preferably disconnected during the predetermined delay time to interrupt power dissipation therein. Therefore, the first or second resistive pattern, which is thermally connected to the upper and lower wall structures of the heat exchanger, will attain substantially the same temperature as said wall structures. The temperature of the upper and lower wall structures converge towards the temperature of the infusion fluid in the fluid channel or passage during the predetermined delay time. Thus, the temperature of the infusion fluid in the fluid channel or passage can be indirectly determined. The predetermined delay time will improve the accuracy of the temperature determination or measurement.

In a further embodiment of the present infusion fluid warmer, the controller is configured for selectively connecting and disconnecting the DC power supply input to the first or second resistive patterns over time to control the temperature of the infusion fluid in accordance with the setpoint temperature or target temperature of the infusion fluid.

In a further embodiment of the infusion fluid warmer, each of the upper wall structure and lower wall structure of the heat exchanger is composed of a material having a thermal conductivity equal to or exceeding 15 W/(m·K) or equal to or exceeding 200 W/(m·K).

The higher the thermal conductivity the more efficient is the conducting of power in the form of heat from the first and/or second resistive pattern(s) to the infusion fluid through the upper and lower wall structures, respectively.

Materials included above are metallic materials, for example aluminium and non-metallic materials, for example thermally conductive polymers.

The effect of this is that the temperature difference between the first and/or second resistive pattern(s) and the infusion fluid can be lowered during power dissipation in the first and/or second resistive pattern(s).

An exemplary embodiment the infusion fluid warmer is configured with a target temperature of the infusion fluid of 39° C.±3° C. and a maximum temperature of the first and/or second resistive pattern at or below 42° C. during power dissipation therein. This embodiment adds a fail-safe feature of the fluid warmer if the infusion fluid supply is interrupted. For example, in case the fluid flow is suddenly interrupted the temperature of the infusion fluid held in the heat exchanger will increase to the temperature of the upper and lower wall structures of the heat exchanger to attain thermal equilibrium. The temperature of the upper and lower wall structures is below a temperature that may cause injury to the patient if infusion fluid with the temperature of the upper and lower wall structures is injected into the patient. Therefore the interruption of the flow of infusion fluid and a subsequent recommencement of infusion fluid flow is safe to the patient.

Moreover, the temperature measurement during the second time period becomes more responsive and accurate as the conductivity is increased.

In an embodiment the upper and lower wall structures are made of stainless steel having a thermal conductivity of approximately 16 W/(m·K).

In an embodiment the upper and lower wall structures of the heat exchanger are made of a thermally conductive polymer having a thermal conductivity of approximately 20 W/(m·K).

In an embodiment the upper and lower wall structures of the heat exchanger are made of aluminium having a thermal conductivity of approximately 205 W/(m·K).

The aluminium may be anodized to provide electrical insulation between the first resistive pattern and the upper wall structure and electrical insulation between the second resistive pattern and the lower wall structure. Herewith a thin layer of aluminium oxide is applied to the surface of the upper and lower wall structures. The aluminium oxide layer has a thermal conductivity of approximately 30 W/(m·K).

In a further embodiment of the infusion fluid warmer, the outer surface of the upper wall structure and the outer surface of the lower wall structure of the metallic heat exchanger comprises a layer or a sheet of electrically insulating material such as Aluminium oxide ($Al_2O_3$) Aluminum Nitrate or Beryllium Oxide layer to electrically insulate the metallic heat exchanger from the first and second integrally formed electrically resistive patterns.

Aluminum oxide is a bio-compatible ceramic material. Therefore direct contact with the infusion fluid to be distributed to a patient is allowable.

Certain embodiments of the infusion fluid warmer may comprise an electrically insulating frame, gasket or ring surrounding and contacting peripheral edges of the upper and lower wall structures of the metallic heat exchanger to comply with various official electrical safety standards for medical equipment. According to this embodiment, the infusion fluid warmer further comprises:
  an outer housing or casing surrounding and enclosing at least the heat exchanger, the first printed circuit board and the second printed circuit board; and
  an electrically insulating frame, gasket or ring surrounding and contacting peripheral edges of the upper and lower wall structures of the metallic heat exchanger to prevent physical contact and electrical contact between the heat exchanger and the outer housing.

The electrically insulating frame, gasket or ring may comprise an elastomeric agent or composition such as silicone or rubber and may be arranged in-between the heat exchanger and an outer casing shell or housing shell of the fluid warmer to avoid physical contact and/or electrical connection between these items. This arrangement of the electrically insulating frame, gasket or ring around the heat exchanger may provide an additional electrically insulating barrier between the infusion fluid and the outer casing or housing of the infusion fluid warmer to enhance its AC mains insulation.

In a further embodiment of the present infusion fluid warmer the upper wall structure and the lower wall structure of the metallic heat exchanger has a plate shaped structure with a thickness over the fluid channel or passage of less than 5 mm or less than 3 mm.

The thickness of the upper wall structure or lower wall structure over the fluid channel or passage is a trade-off between ensuring the structural integrity and support the thermal conduction through the wall structures.

Ensuring the structural integrity require a certain thickness. Thermal conduction through the wall structure is increased with decreased thickness. A thickness of less than 5 mm or less than 3 mm is a good compromise and has shown good heat flow, when applying power to the resistive pattern and good responsiveness during temperature measurement when the power supply to the resistive pattern is interrupted.

In a further embodiment of the infusion fluid warmer according to the invention, a width-to-thickness ratio of the fluid channel or passage is at least 50:1 or at least 175:1 or at least 350:1.

In a further embodiment of the infusion fluid warmer according to the invention, a thickness of the fluid channel or passage is between 0.1 mm and 0.5 mm or approximately 0.2 mm.

The fluid channel or passage may have various outlines.

In an embodiment the fluid channel or passage can be divided into three zones. The first being an inlet transition zone, the second being a central zone and the third being an outlet transition zone.

In the inlet transition zone the outline of the fluid channel or passage transitions from a width corresponding to the diameter of the fluid inlet to a width corresponding to the width of the central zone in a triangular shape. The thickness of the fluid channel or passage in the inlet transition zone decrease from a thickness corresponding to the diameter of the fluid inlet to a thickness corresponding to the thickness of the central zone also in a triangular shape.

In the central zone the width and thickness of the fluid channel or passage is unchanged towards the outlet transition zone.

In the outlet transition zone the width of the fluid channel or passage decrease, the thickness is unchanged over a triangular shape until the fluid outlet is reached. Here the outline changes to a circular shape.

In the embodiment described above, the cross sectional area of the central zone is less than the cross sectional area of the fluid inlet and outlet, respectively. In the central zone of said embodiment the width-to-thickness ratio of the fluid channel is approximately 175:1 and the thickness is approximately 0.2 mm. This result in a relatively thin film of infusion fluid in the fluid channel or passage compared to the width. Therefore the infusion fluid in the fluid channel or passage is exposed to a relatively high amount of dissipated heat per volume. Thus, the infusion fluid only requires traveling a relatively short distance longitudinally in the fluid channel before the infusion fluid has been heated to the set temperature.

In an embodiment of the infusion fluid warmer the outline of the first and second resistive pattern corresponds to the outline of the fluid channel or passage. This embodiment achieves that the amount of power dissipated from the first and second resistive pattern can be maximized.

In a further embodiment of the infusion fluid warmer the controller and/or switching circuit is bonded or soldered to the first surface of the first printed circuit board or bonded or soldered to the first surface of the second printed circuit board.

The controller is then mounted on the printed circuit board of the infusion fluid warmer. Moreover, the distance from the controller and/or switching circuit to the resistive patterns can be as short as possible to limit losses due to resistance in the circuit.

In a further embodiment of the infusion fluid warmer according to the invention, the first printed circuit board further comprises:
- at least one additional and separate integrally formed electrically resistive patterns formed on the second surface and/or wherein the second printed circuit board further comprises:
- at least one additional and separate integrally formed electrically resistive patterns formed on the second surface.

By introducing additional resistive patterns in the first and second printed circuit boards the maximum power dissipated in each resistive pattern can be reduced to protect the power supply and limit the maximum temperature of the resistive pattern during power dissipation.

In an embodiment of the infusion fluid warmer, a resistance of each additional electrically resistive pattern is less than 11 Ω such as between 1 and 7Ω.

The additional resistive patterns may vary in size and resistance.

In a further embodiment of the infusion fluid warmer the heat exchanger comprises a fluid inlet port and a fluid outlet port arranged at first and second opposing ends, respectively, of the longitudinally extending fluid channel or passage.

In a further embodiment of the present infusion fluid warmer the first integrally formed electrically resistive pattern and said at least one additional and separate integrally formed electrically resistive patterns are arranged sequentially along the second surface of the first printed circuit board; and/or wherein the second integrally formed electrically resistive pattern and the one or more additional and separate integrally formed electrically resistive patterns are arranged sequentially along the second surface of the second printed circuit board.

In a further embodiment of the infusion fluid warmer the electronic switching circuit further comprises:
- a first controllable semiconductor switch coupled in series between the DC power supply input and the first integrally formed electrically resistive pattern and a first reference resistor connected across input and output terminals of the first controllable semiconductor switch; and
- a second controllable semiconductor switch coupled in series between the DC power supply input and the second integrally formed electrically resistive pattern and a reference resistor connected across input and output terminals of the second controllable semiconductor switch.

The resistance of each of the first and second reference resistors may be at least 100 times larger than an on-resistance of each of the first and second controllable semiconductor switches.

In a further embodiment of the infusion fluid warmer according to the invention, the electronic switching circuit further comprises a plurality of additional controllable semiconductor switches coupled to the controller and configured for:
- selectively connecting and disconnecting said at least one additional and separate integrally formed electrically resistive patterns of the first printed circuit board to the DC power supply input; and/or
- selectively connecting and disconnecting each of the said at least one additional and separate integrally formed electrically resistive patterns of the second printed circuit board to the DC power supply input.

The connecting and disconnecting is based on the determined temperature and the available power from the power supply.

In a further embodiment of the infusion fluid warmer according to the invention, the controller is further configured for:
- connecting and disconnecting over time the first and said at least one additional integrally formed electrically resistive patterns of the first printed circuit board to the DC power supply input,
- connecting and disconnecting over time the second and said at least one additional integrally formed electrically resistive patterns of the second printed circuit board to the DC power supply input,
- determining a resistance of any of said first, second or additional resistive patterns during a second time period, and
- determining a temperature of any of said first, second or additional resistive patterns based on the resistance determination.

A separate, second, invention has been found in an infusion fluid warmer comprising:
- a DC power supply input,
- a first carrier board comprising a first surface and a second, opposing, surface, wherein the second surface comprises a first plurality of separate integrally formed electrically resistive patterns,
- a second carrier board comprising a first surface and a second, opposing, surface, wherein the second surface comprises a second plurality of separate integrally formed electrically resistive patterns,
- a heat exchanger comprising an upper wall structure and a lower, opposing, wall structure separated by a fluid channel or passage extending between fluid inlets and outlets of the heat exchanger, and
- a controller for connecting the DC power supply input to the first plurality and/or second plurality of integrally formed electrically resistive patterns, wherein, an outer surface of the upper wall structure is thermally connected to the first plurality of resistive patterns and an outer surface of the lower wall structure is thermally connected to the second plurality of resistive patterns, and that the controller is configured to:
- selectively connecting over time the DC power supply input to a resistive pattern selected among the first plurality and/or the second plurality of integrally formed electrically resistive patterns during a first time period to dissipate power in the selected resistive pattern,
- determining a resistance of the selected resistive pattern, and
- determining a temperature of the selected resistive pattern based on the resistance determination.

In a further embodiment of the infusion fluid warmer the first plurality of integrally formed electrically resistive patterns are arranged sequentially along the second surface of the first printed circuit board; and wherein the second plurality of integrally formed electrically resistive patterns are arranged sequentially along the second surface of the second printed circuit board.

The temperature may be determined for each electrically resistive pattern of the first plurality and second plurality of integrally formed electrically resistive patterns. Based on these measurements the controller may connect the DC power supply input to resistive patterns selected among the first plurality and each of the second plurality of integrally formed electrically resistive patterns according to which of the resistive patterns that may be in deficit in relation to the target temperature.

The controller may prioritise connecting the DC power supply input to resistive patterns close to the fluid outlet as it may be advantageous to secure that infusion fluid has the intended or target temperature at the outlet of the fluid channel.

The skilled person will understand that the various functions and features discussed above in connection with the description of the first aspect of the infusion fluid warmer comprising may be incorporated in a corresponding manner in the infusion fluid warmer according to the second invention.

It should be emphasized that the term "comprises/comprising/comprised of" when used in this specification is taken to specify the presence of stated features, integers, steps or components but does not preclude the presence or addition of one or more other features, integers, steps, components or groups thereof.

BRIEF DESCRIPTION OF THE DRAWINGS

Various embodiments of the invention will be explained in more detail below with reference to the accompanying drawings, wherein.

In the following, the invention will be described in greater detail with reference to embodiments shown by the enclosed figures. It should be emphasized that the embodiments shown are used for example purposes only and should not be used to limit the scope of the invention.

DESCRIPTION OF EMBODIMENTS

In the explanation of the figures, identical or corresponding elements will be provided with the same designations in different figures. Therefore, no explanation of all details will be given in connection with each single figure/embodiment.

Figure 1:
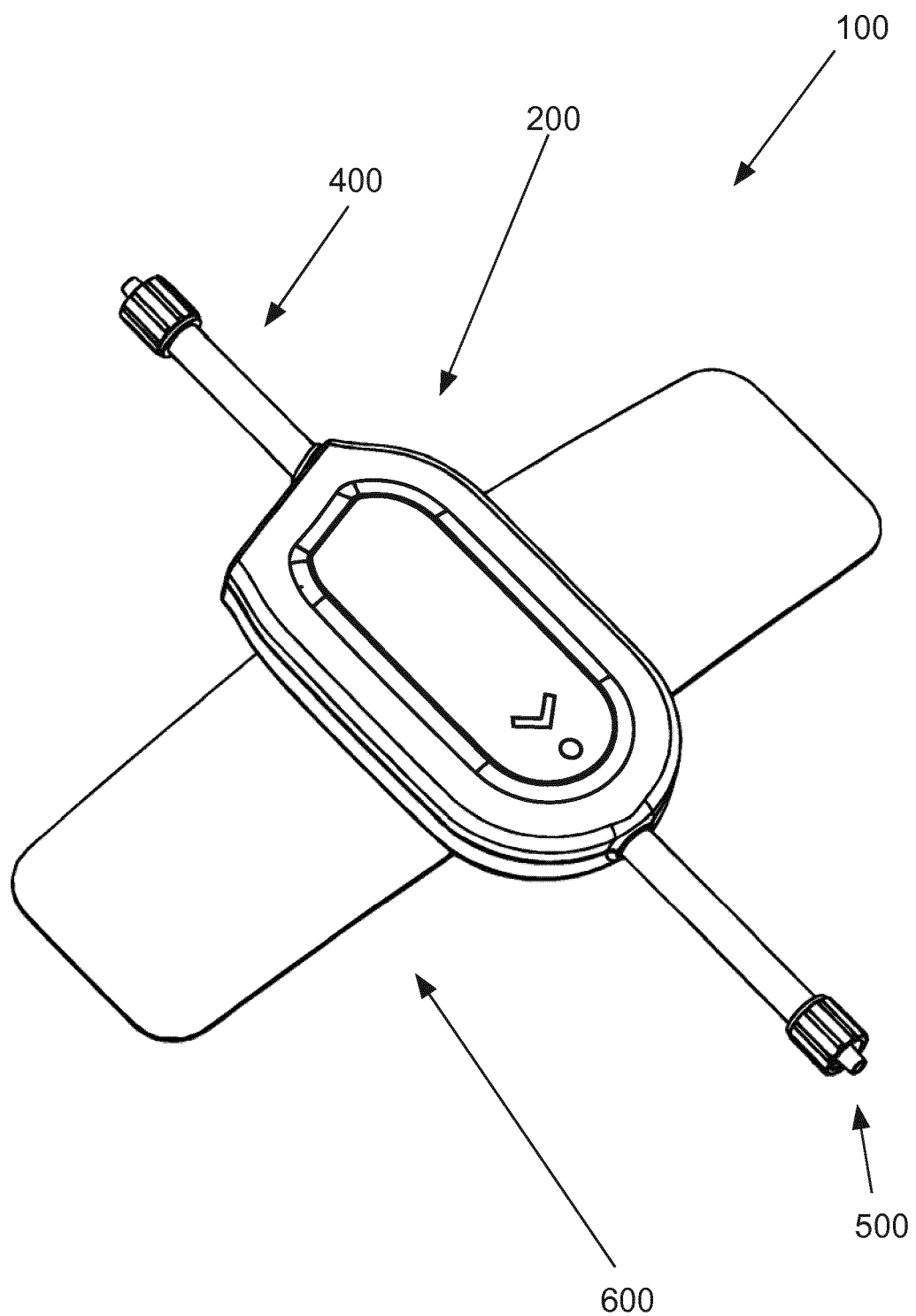
FIG. 1 shows an illustration of an infusion fluid warmer.
Figure 2:
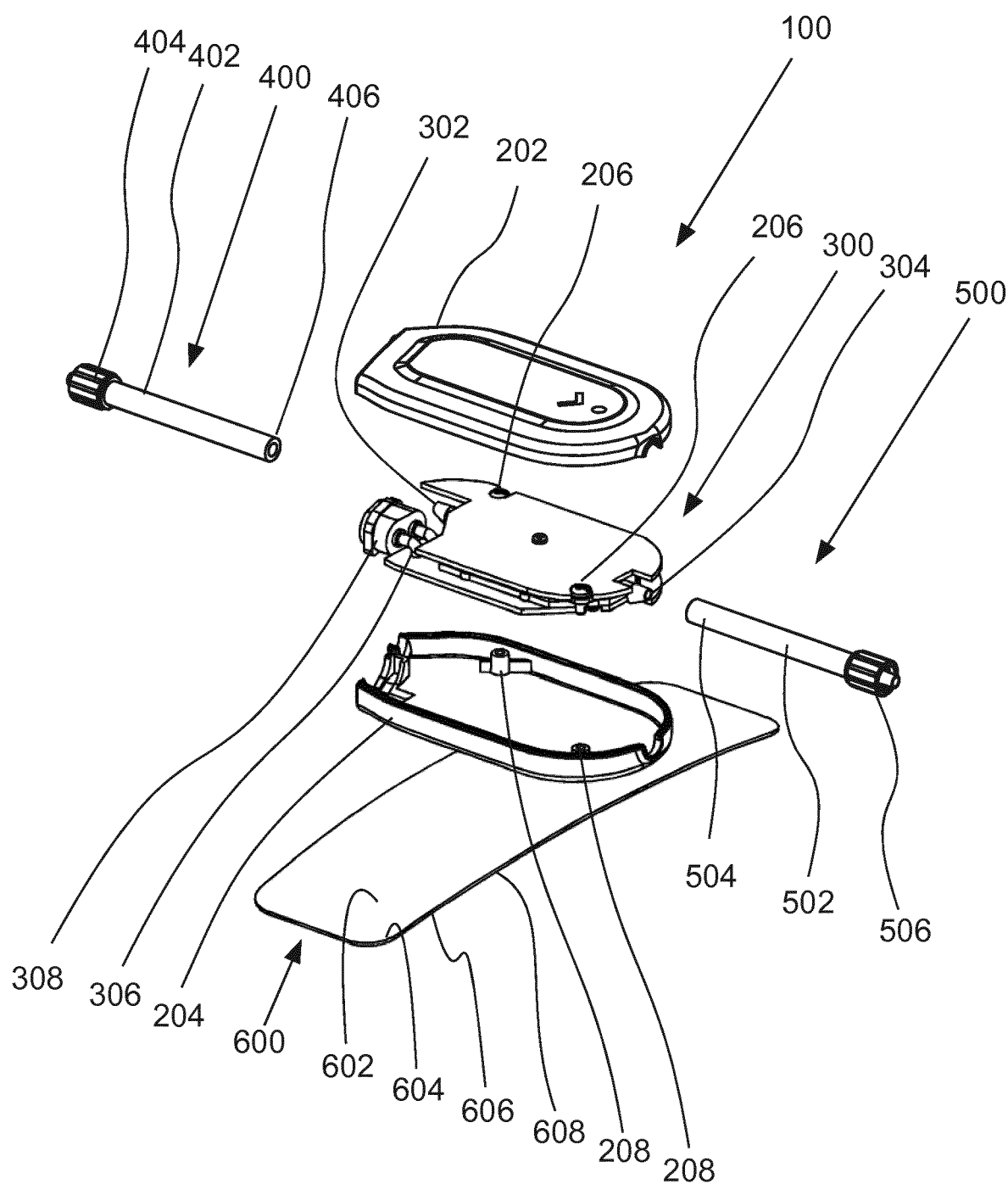
FIG. 2 is an exploded view of the infusion fluid warmer of FIG. 1, showing the main components.

FIG. 1 shows an illustration of an infusion fluid warmer 100 according to the invention and FIG. 2 shows an exploded view of the main components of the infusion fluid warmer of FIG. 1.

The infusion fluid warmer 100 comprises an outer casing 200, a heating unit 300, see FIG. 2, an inlet tube unit 400, an outlet tube unit 500 and an attachment unit 600.

The infusion fluid warmer 100 is configured for being placed or attached directly onto a patients arm or other parts of the body. Therefore its size and weight is restricted by this requirement.

The outer casing 200 provides support for- and protection of the components of the infusion fluid warmer 100. Moreover, the outer casing 200 provides electrical insulation and some thermal insulation of the heating unit 300, such that the patient is protected from electrical shock and such that the electrical components are protected from damage due to for example electrostatic discharge (ESD). The heating unit 300 preferably operates at temperatures that are sufficiently low, for example below 42 degree C., to avoid burns. Therefore the thermal insulating capabilities of the outer casing 200 may be of secondary importance.

The outer casing 200 comprises an upper shell 202 and a lower shell 204. In the embodiment shown the upper shell 202 and the lower shell 204 respectively is formed with internal supports that complements the shape of the heating unit 300, the inlet tube unit 400 and the outlet tube unit 500 when installed in the outer casing 200 such that said units are held in a firm form-fit attachment to the outer casing 200, when the upper shell 202 and the lower shell 204 are mated.

In the embodiment shown the heating unit 300 is attached to the lower shell 204 by two screws 206 that are inserted through the heating unit 300 into studs 208 with holes formed in the lower shell 204.

In one embodiment the holes are threaded to match machine screws

In a further embodiment the holes are unthreaded to match self-tapping screws.

In the embodiment shown the upper shell 202 and the lower shell 204 are injection moulded plastic parts.

Alternatively the upper shell 202 and lower shell 204 can be formed in other suitable ways, for example by milling, casting or 3D printing.

The heating unit 300 is configured for heating to a required temperature, an infusion fluid that flows through the heating unit 300 to be used for intravenous therapy in a patient.

The infusion fluid enters the heating unit 300 through a fluid inlet port 302 that is in communication with the inlet tube unit 400 and exits through a fluid outlet port 304 that is in communication with the outlet tube unit 500.

Figure 4:
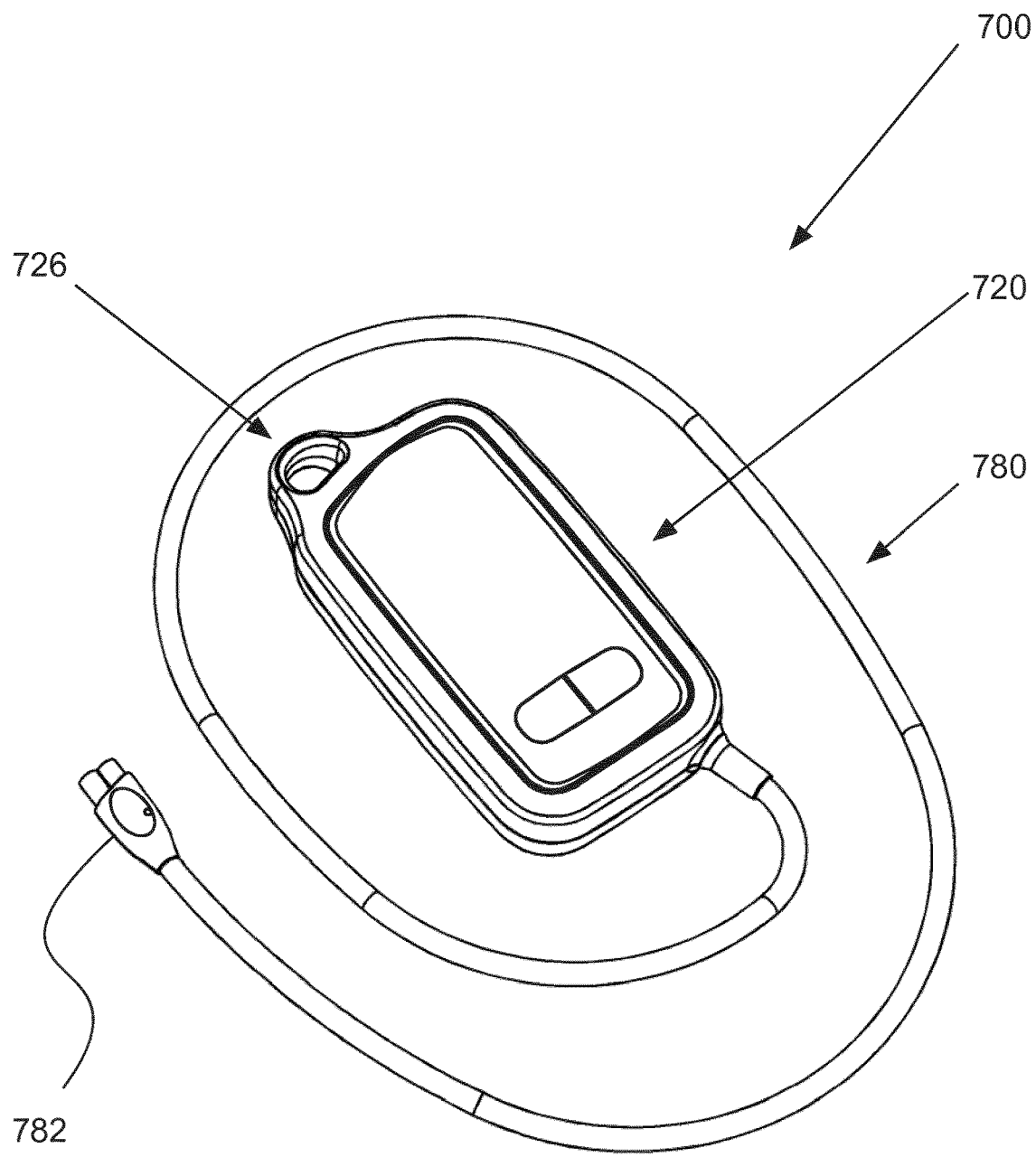
FIG. 4 shows an illustration of a power supply unit for the infusion fluid warmer of FIG. 1.
Figure 5:
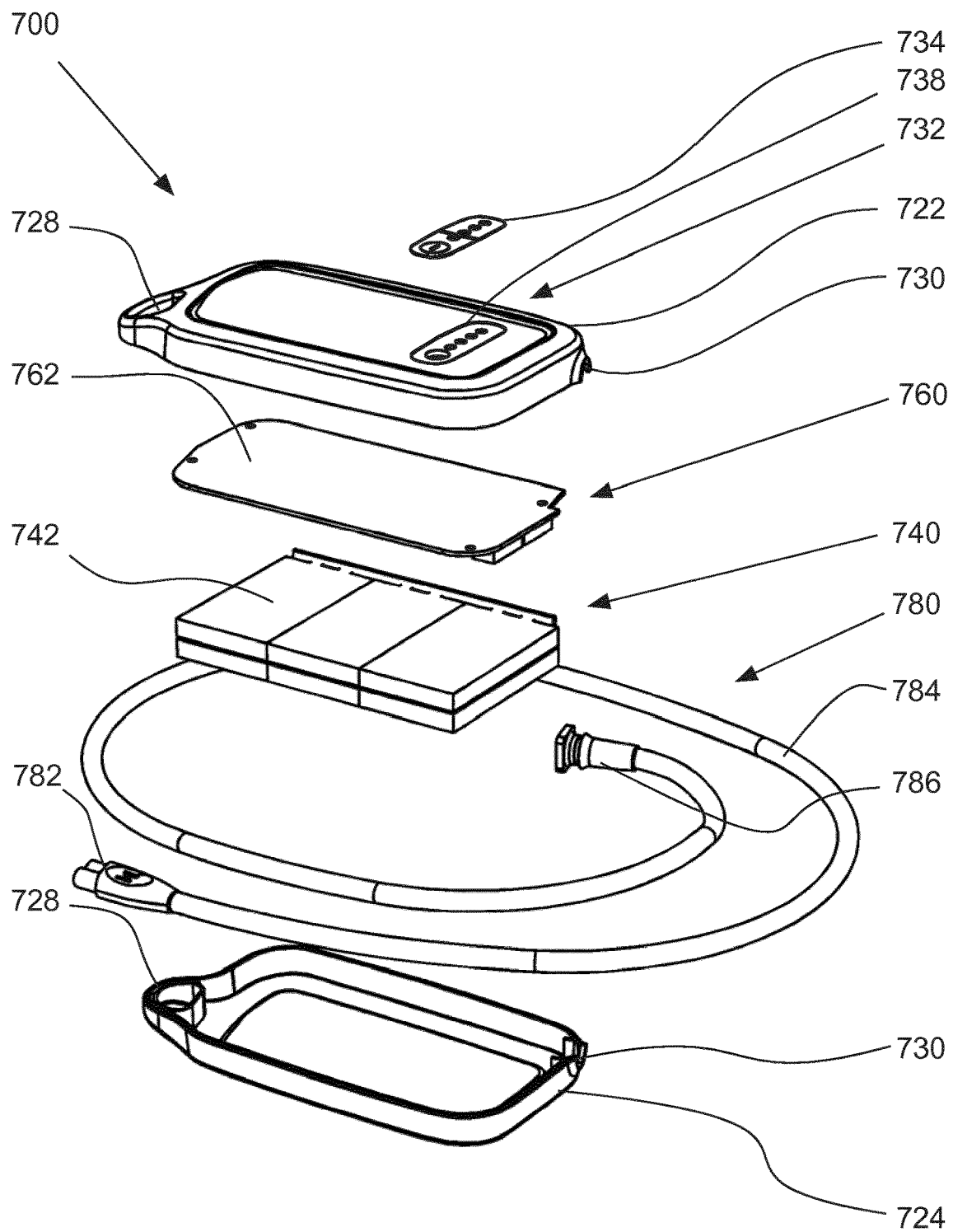
FIG. 5 shows an exploded view of the main components of the power supply of FIG. 4.

The heating unit 300 is electrically powered through a DC power supply input 306 that is in communication with a receptacle 308 configured for receiving a power plug 782 of a power supply 700, see FIGS. 4 and 5.

Figure 3:
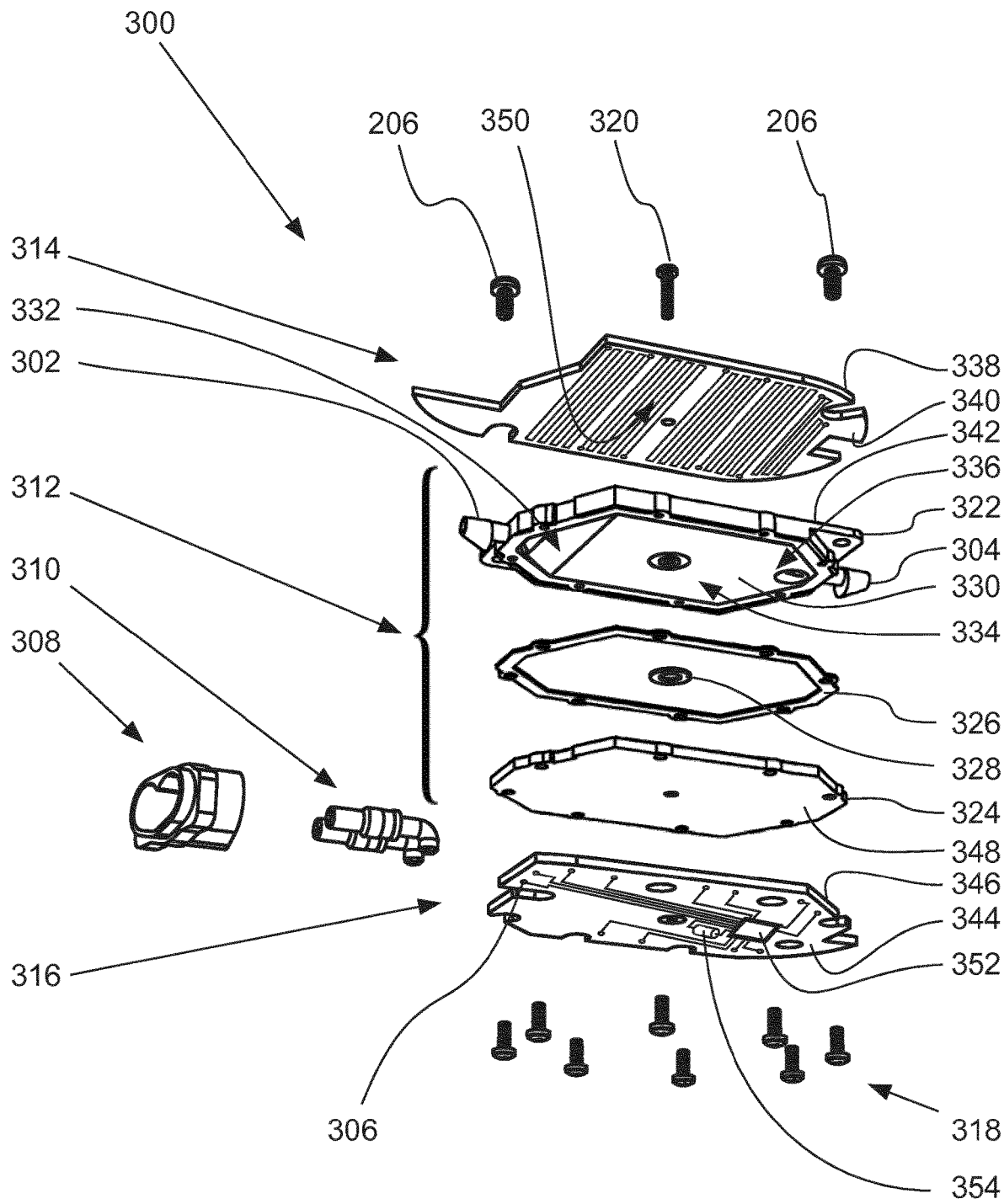
FIG. 3 shows an exploded view of a heating unit of the infusion fluid warmer of FIG. 1.

The heating unit 300 is further described in FIG. 3.

The inlet tube unit 400 is a plastic tube 402 having a luer type connector 404 at its first end configured for connection of the inlet tube unit 400 to a supply of intravenous fluid. The second end of the plastic tube 402 is configured for fitting onto the fluid inlet port 302 of the heating unit 300. The fluid inlet port 302 comprises a barbed fitting for providing a leak tight connection to the tube 402.

The outlet tube unit 500 is a plastic tube 502 connected at its first end 504 to the fluid outlet port 304 of the heating unit 300. The fluid outlet port 304 comprises a barbed fitting for providing a leak tight connection to the tube 502. The second end of the plastic tube 502 is having a luer type connector 506 that is configured for connection of the outlet tube unit 500 to an intravenous access device, for example a catheter.

The plastic tubes 402, 502 are made of a flexible plastic material.

The attachment unit 600 is configured for attachment of the infusion fluid warmer 100 directly to the patient or a support arrangement in the vicinity of the patient.

In the embodiment shown the attachment unit 600 comprises an adhesive patch 602 that attaches the infusion fluid warmer 100 directly on the skin of the patient.

In a first embodiment of the attachment unit 600 the adhesive patch 602 comprises an upper adhesive layer 604 that adheres to the lower shell 204 of the infusion fluid warmer 100, a lower adhesive layer 606 that is configured for adhering to the skin of a patient and a carrier layer 608 separating the upper and lower adhesive layers 604, 606.

The upper adhesive layer 604 can be composed of any adhesive suitable for attaching the adhesive patch 602 to the infusion fluid warmer 100, for example an acrylic.

The lower adhesive layer 606 shall be composed of a medical grade adhesive, for example a medical grade silicone adhesive. The carrier layer is configured for preventing collapsing or wrinkling of the adhesive layers 604, 606. In an embodiment the carrier layer 608 is a foam layer. The carrier layer 608 can also be a textile or a film layer.

In a second embodiment (not shown), the attachment unit 600 comprises an adhesive patch with an outline corresponding to the outline of the lower shell 204 of the outer casing 200. The adhesive patch is composed of an upper adhesive layer for attaching the adhesive patch to the infusion fluid warmer 100 and a lower adhesive layer for attaching the adhesive patch to the patient.

The upper adhesive layer can be composed of any adhesive suitable for attaching the adhesive patch to the infusion fluid warmer 100, for example an acrylic. The lower adhesive layer shall be composed of a medical grade adhesive, for example a medical grade silicone adhesive, a hydrogel or a medical grade acrylic adhesive.

In this embodiment the lower shell 204 acts to prevent the collapsing and wrinkling of the adhesive layers.

FIG. 3 shows an exploded view of a heating unit 300 of the infusion fluid warmer 100 of FIG. 1.

The heating unit 300 comprises a receptacle 308 with connector pins 310, a heat exchanger 312, a first printed circuit board 314 hereinafter referred to as the first PCB, a second printed circuit board 316 hereinafter referred to as the first PCB, a plurality of heat exchanger assembly screws 318 and a heating unit assembly screw 320.

The receptacle 308 is described above.

The connector pins 310 interface with corresponding sockets in the power plug 782 of the power supply 700, see FIGS. 4 and 5. The connector pins 310 are in electrical contact with the DC power supply input 306 on the second PCB 314.

The heat exchanger 312 comprises an upper wall structure 322 and an opposing lower wall structure 324. A peripheral gasket 326 and a central gasket 328 is located between the upper wall structure 322 and the lower wall structure 324 to seal the fluid channel 331 and thereby prevent leakage of infusion fluid flowing through the heat exchanger 312. The infusion fluid warmer may comprise an electrically insulating frame or ring (not shown) surrounding and contacting peripheral edges of the upper and lower wall structure 322, 324. The electrically insulating frame or ring may comprise an elastomeric agent or composition such as rubber and may be arranged in-between the heat exchanger 312 and the outer casing 200 to avoid physical contact between these items. This optional arrangement of the electrically insulating frame or ring around the heat exchanger 312 provides an additional electrically insulating barrier between the infusion fluid and the outer casing 200 of the infusion fluid warmer to enhance its mains insulation. This arrangement of two separate electrically insulting barriers may be advantageous, or even mandatory, to comply with various official safety standards for medical equipment.

The upper wall structure 322 of the heat exchanger 312 is an elongate plate shaped member that has a fluid inlet port 302 at one end and a fluid outlet port 304 at its other end. A cavity 330 is formed in the upper wall structure 322. The cavity 330 extends between the fluid inlet port 302 and the fluid outlet port 304 of the heat exchanger 312. The cavity 330, together with the peripheral gasket 326 and the central gasket 328, defines the fluid channel 331 or passage, see FIG. 6-8 in the longitudinal direction of the heat exchanger 312 for the infusion fluid.

The flow path comprises three zones. The first zone is an inlet transition zone 332, where the cross section of the cavity 330 in a plane perpendicular to the longitudinal direction of the heat exchanger 312 transitions from a circular cross section to a polygonal cross section. The second zone is a central zone 334, where the cross section of the cavity 330 is unchanged from the polygonal cross section apart from the location of the heating unit assembly screw 320 and associated central gasket 328, where it changes to two separate polygons. In the embodiment shown the polygon has four sides and forms a rectangle. Cavity 330 is formed such that the polygon in the central zone has two opposing long sides facing the first and second PCBs 314, 316 respectively, and two opposing short sides where the long sides are significantly longer than the short sides. The third zone is an outlet transition zone, where the cross section of the cavity 330 transitions from a polygonal cross section to a circular cross section to interface with the fluid outlet port 304.

In the embodiment shown the thickness of the fluid channel is 0.2 mm. The width of the fluid channel is approximately 35 mm and the length approximately 60 mm. Thus, the width to thickness ratio of the fluid channel 331 in the central zone 334 is approximately 175:1.

The upper wall structure 322 has a plane bearing surface for the peripheral gasket 326 and the central gasket 328.

The lower wall structure 324 is a plane plate shaped member with an outline corresponding to the outline of the upper wall structure 322.

The lower wall structure 324 has a plane bearing surface for the peripheral gasket 326 and the central gasket 328.

The heat exchanger 312 is assembled by inserting the peripheral gasket 326 and the central gasket 328 between the upper and lower wall structures 322, 324 before said wall structures are moved together.

The heat exchanger assembly screws 318 are inserted through holes in the lower wall structure 324 into threaded holes in the upper wall structure 322. The heat exchanger assembly screws 318 are tightened to ensure a leak-proof flow path inside the heat exchanger 312.

The upper and lower wall structures 322, 324 are made of aluminium that has a high thermal conductivity.

The aluminium of the upper and lower wall structures is preferably passivated through anodizing. This adds a layer of aluminium oxide ($Al_2O_3$) to the surface of the aluminium. This aluminium oxide layer is bio-compatible and therefore the infusion fluid is allowed direct contact with the anodized surface of the upper and lower wall structures 322, 324 prior to distribution to the patient.

The anodizing provides good corrosion resistance of the aluminium. Moreover the aluminium oxide layer is electrically non-conductive. The thermal conductivity of the aluminium oxide layer is reduced in comparison to aluminium, but because the layer may be very thin, this has no noticeable effect on the operation of the heating unit 300.

The peripheral gasket 326 and the central gasket 328 are made of silicone, for example medical grade silicone.

The first PCB 314 has a first surface 338 and an opposing second surface 340. When installed into the heating unit 300 the second surface 340 is placed in contact with an outer surface 342 of the upper wall structure 322 of the heat exchanger 312. The second surface 340 of the first PCB 314 is plane to complement the shape of the outer surface 342 of the upper wall structure to ensure good contact across the surface. In addition, a layer of thermally conductive paste or film is added between the first PCB 314 and the upper wall structure 322 to ensure a good thermal connection or coupling between the two parts.

The second PCB 316 has a first surface 344 and an opposing second surface 346. When installed into the heating unit 300 the second surface 346 is placed in contact with an outer surface 348 of the lower wall structure 324 of the heat exchanger 312. The second surface 346 of the first PCB 314 is plane to complement the shape of the outer surface 348 of the lower wall structure to ensure good contact across the surface. In addition, a layer of thermally conductive paste or film is added between the second PCB 316 and the lower wall structure 324 to ensure good thermal coupling or connection between the two parts.

The first and second PCBs 314, 316 each has an electrically resistive pattern 350. In FIG. 3 the electrically resistive pattern on the second PCB 316 is hidden from view. However, the electrically resistive pattern on the second PCB 316 is similar to the electrically resistive pattern 350 on the first PCB 314 that is visible in FIG. 3.

In the embodiment shown the first and second PCBs 314, 316 the electrically resistive pattern each comprises five separate and integrally formed electrically resistive patterns formed on their respective second surfaces 340, 346.

In the embodiment shown, the electrical components that control the application of power to the electrically resistive pattern 350 is located on the first surface 344 of the second PCB 316. This includes a controller 352 in the form of an integrated circuit (IC) and a reference resistor 354.

The controller 352 is configured for controlling the application of power to the electrically resistive pattern 350 on the first and second PCBs 314, 316 and for determining the resistance in the electrically resistive pattern 350.

When power is applied to the electrically resistive pattern 350, power is dissipated in the material making up the electrically resistive pattern 350 to produce heat. Due to the resistive pattern 350 being in thermal contact with the outer surface 342, 348 of the upper and lower wall structure 322, 324 of the heat exchanger 312 the temperature of the upper and lower wall structure 342, 348 will rise in the vicinity of the powered resistive pattern 350. The temperature of the infusion fluid flowing through the fluid channel 331, see FIG. 6-8 will thus be elevated between the fluid inlet port 302 and the fluid outlet port 304.

Due to the ratio of width to height of the fluid channel of 175:1 as previously mentioned, the area of the electrically resistive pattern 350 which, when power is applied, acts as a heater or heating element is relatively high in relation to the thickness of the fluid channel. Moreover, due to the small height of the fluid channel, the heating of the infusion fluid is rapid. The skilled person will, based on the laws of thermodynamics, appreciate that it is possible to dissipate a relatively high amount of power to the infusion fluid with a relatively low temperature increase of the heat exchanger surfaces. Therefore the temperature of the heat exchanger structure is close to the temperature of the infusion fluid.

FIG. 4 shows an illustration of a power supply unit 700 for the infusion fluid warmer 100 of FIG. 1 and FIG. 5 shows an exploded view of the main components of the power supply of FIG. 4.

The power supply unit 700 comprises a power supply casing 720, a battery pack 740, a power supply controller 760 and a power cable assembly 780.

The power supply casing 720 provides support for and protection of the components within the power supply unit 700. Additionally, the power supply casing 720 provides electrical insulation, such that the personnel is protected from electrical shock and such that the electrical components are protected from damage due to for example electrostatic discharge (ESD).

The power supply casing 720 comprises a front shell 722 and a back shell 724. When assembled an eye 726 is formed by complementary apertures 728 in the front and back shell, respectively for hanging the power supply unit 700 from an IV stand, for example with a hook or a web through the eye 726.

The front shell 722 and back shell 724 are formed with cut-outs 730 that each forms half of an opening when the front and back shells 722, 724 are assembled.

The back shell 724 and optionally the front shell 722 each are formed with a non-slip material (not shown) over part of its surface. The non-slip material is a thermoplastic elastomer (TPE) or a rubber material.

The front shell 722 is formed with a plurality of small openings 732 providing a visible access to the LEDs that provide status information. A foil label 734 is provided to cover the openings 732. A recess 738 having an outline corresponding to the outline of the label 734 and a depth corresponding to the thickness of the label is formed on the outside of the front shell 722. The foil label 734 has transparent or semi-transparent windows aligned with the LEDs, such that the openings 732 into the internal of the power supply casing 720 are closed while at the same time the LEDs are visible through the windows and able to provide status information to the personnel.

In an embodiment not shown the infusion fluid warmer 100 comprise audible alarming means for audibly providing status and alarms.

In the embodiment shown the front shell 722 and the back shell 724 are injection moulded plastic parts that are moulded in a 2K moulding process where two materials are introduced during the moulding process.

First a mixture of polycarbonate and acrylnitrile-butadiene-styrene (PC-ABS) is introduced into the mould to form the shell. Then a thermoplastic elastomer is introduced to form the non-slip surface over part of the shell.

The front shell 722 and back shell 724 are connected through ultrasonic welding.

The battery pack 740 comprises a plurality of battery cells 742, for example lithium polymer (Li—Po) or lithium ion (Li-Ion).

The power supply controller 760 comprises a printed circuit board (PCB) 762 with a controller configured for providing electrical power at a specified voltage from the battery pack 740 to the power cable assembly 780 and ultimately the infusion fluid warmer 100, configured for providing status information through LEDs that are visible through the front shell 722 and configured for controlling the recharging of the battery pack 740.

The power cable assembly 780 comprises a power plug 782, a cable 784 and a connection means 786 for electrically connecting the cable to the power supply controller 760.

The power plug 782 is configured for being inserted into the receptacle 308 of the infusion fluid warmer 100. The sockets of the power plug 782, when inserted into the receptacle, mates with connector pins 310 and provides an electrical connection between the infusion fluid warmer 100 and the power supply unit 700.

Figure 6:
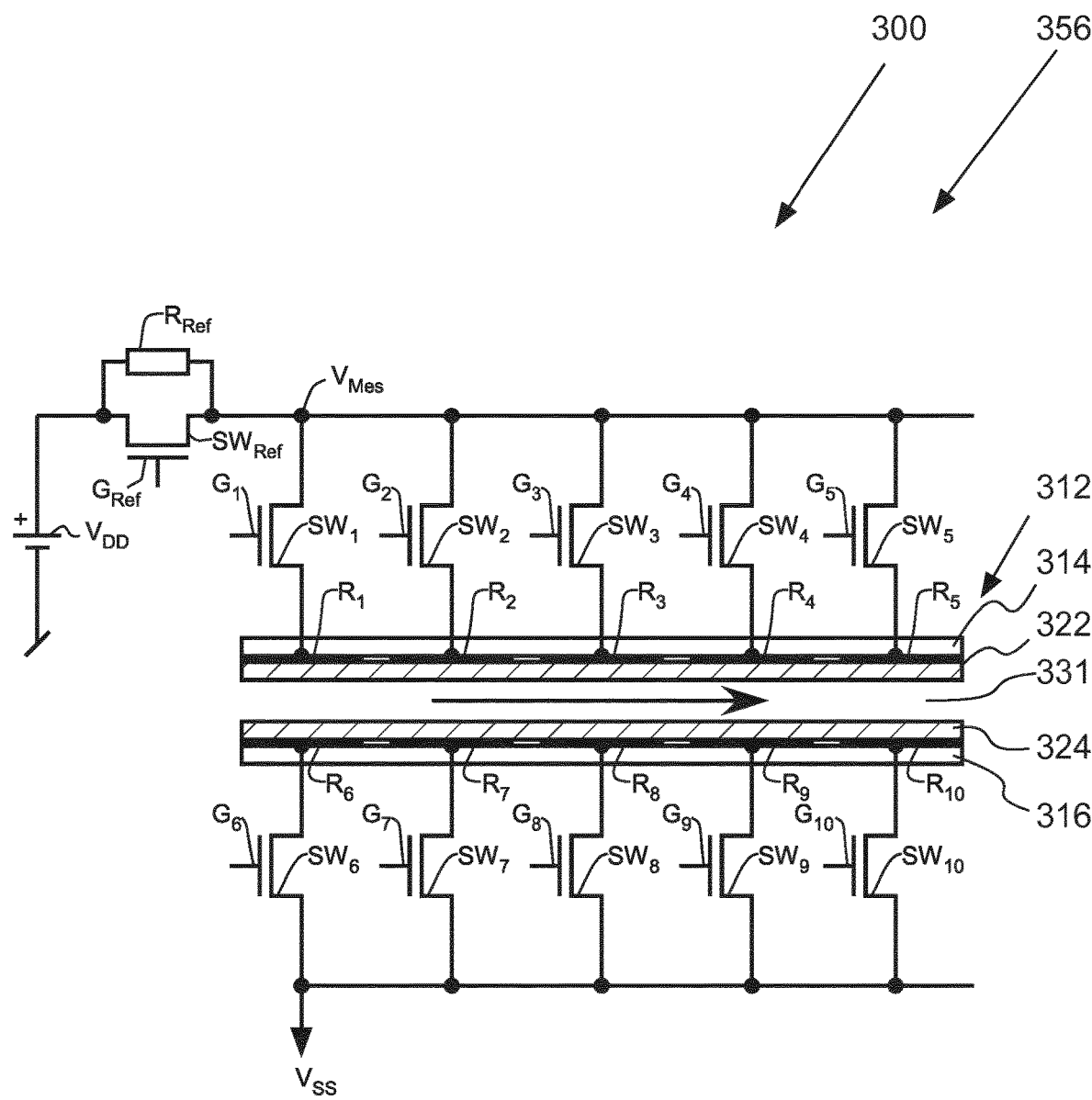
FIG. 6 shows block diagram of the electrical circuit and the heat exchanger of the heating unit.

FIG. 6 shows a simplified schematic block diagram of the electrical circuit 356 and the heat exchanger 312 of the heating unit 300.

In the block diagram only the positive side of the electrical circuit has been shown for simplicity. The skilled person will understand that each of the electrically resistive patterns $R_1, R_2, R_3, R_4, R_5, R_6, R_7, R_8, R_9, R_{10}$ are connected to the negative potential of the DC power supply $V_{DD}$, for example via a ground connection.

The heat exchanger 312 is shown with the associated electrical components. The fluid channel or passage 331 is bound by an upper wall structure 322 with a first PCB 314 attached and a lower wall structure 324 with a second PCB attached 316.

A first integrally formed electrically resistive pattern $R_1$ and four additional and separate integrally formed electrically resistive patterns $R_2, R_3, R_4, R_5$ or simply a plurality of integrally formed electrically resistive patterns are formed on the second surface 340 of the first PCB 314. A second integrally formed electrically resistive pattern $R_6$ and four additional and separate integrally formed electrically resistive patterns $R_7, R_8, R_9, R_{10}$ or simply a plurality of integrally formed electrically resistive patterns are formed on the second surface 346 of the second PCB 316.

An electronic switching circuit is provided that comprises a plurality of controllable semiconductor switches $G_1/SW_1$, $G_2/SW_2$, $G_3/SW_3$, $G_4/SW_4$, $G_5/SW_5$, $G_6/SW_6$, $G_7/SW_7$, $G_8/SW_8$, $G_9/SW_9$, $G_{10}/SW_{10}$ each coupled in series with a respective resistive pattern $R_1, R_2, R_3, R_4, R_5, R_6, R_7, R_8, R_9, R_{10}$. The switches $G_1/SW_1$, $G_2/SW_2$, $G_3/SW_3$, $G_4/SW_4$, $G_5/SW_5$, $G_6/SW_6$, $G_7/SW_7$, $G_8/SW_8$, $G_9/SW_9$, $G_{10}/SW_{10}$ are coupled to a common circuit node $V_{MES}$. Each of the controllable semiconductor switches $G_1/SW_1$, $G_2/SW_2$, $G_3/SW_3$, $G_4/SW_4$, $G_5/SW_5$, $G_6/SW_6$, $G_7/SW_7$, $G_8/SW_8$, $G_9/SW_9$, $G_{10}/SW_{10}$ may comprise a MOSFET such an NMOS or PMOS transistor.

A reference controllable semiconductor switch $G_{Ref}/SW_{Ref}$ is coupled between the DC power supply input $V_{DD}$ and the common circuit node $V_{MES}$. The reference controllable semiconductor switch $G_{Ref}/SW_{Ref}$ may comprise a MOSFET such an NMOS or PMOS transistor. A first reference resistor $R_{Ref}$ is coupled across the input and output terminals of the reference switch $G_{Ref}/SW_{Ref}$. The first reference resistor $R_{Ref}$ may comprise a precision resistor with small tolerance, e.g. less than 1%, and preferably also small temperature coefficient.

In an alternative embodiment the switches $G_6/SW_6$, $G_7/SW_7$, $G_8/SW_8$, $G_9/SW_9$, $G_{10}/SW_{10}$ connected to the second integrally formed electrically resistive pattern $R_6$ and the four additional and separate integrally formed electrically resistive patterns $R_7, R_8, R_9, R_{10}$ formed on the second surface 346 of the second PCB 316 are coupled to a second common circuit node $V_{MES2}$ (not shown). The alternative circuit comprises a second controllable semiconductor switch $G_{Ref2}/SW_{Ref2}$ (not shown) coupled between the DC power supply input $V_{DD}$ and the second common junction point $V_{MES2}$ (not shown). A second reference resistor $R_{Ref2}$ is coupled across the terminals of the second switch $G_{Ref2}/SW_{Ref2}$.

In an embodiment the controller includes a proportional-integral-derivative controller (PID controller) for controlling the power dissipation in each of the electrically resistive patterns $R_1, R_2, R_3, R_4, R_5, R_6, R_7, R_8, R_9, R_{10}$.

Figure 7A:
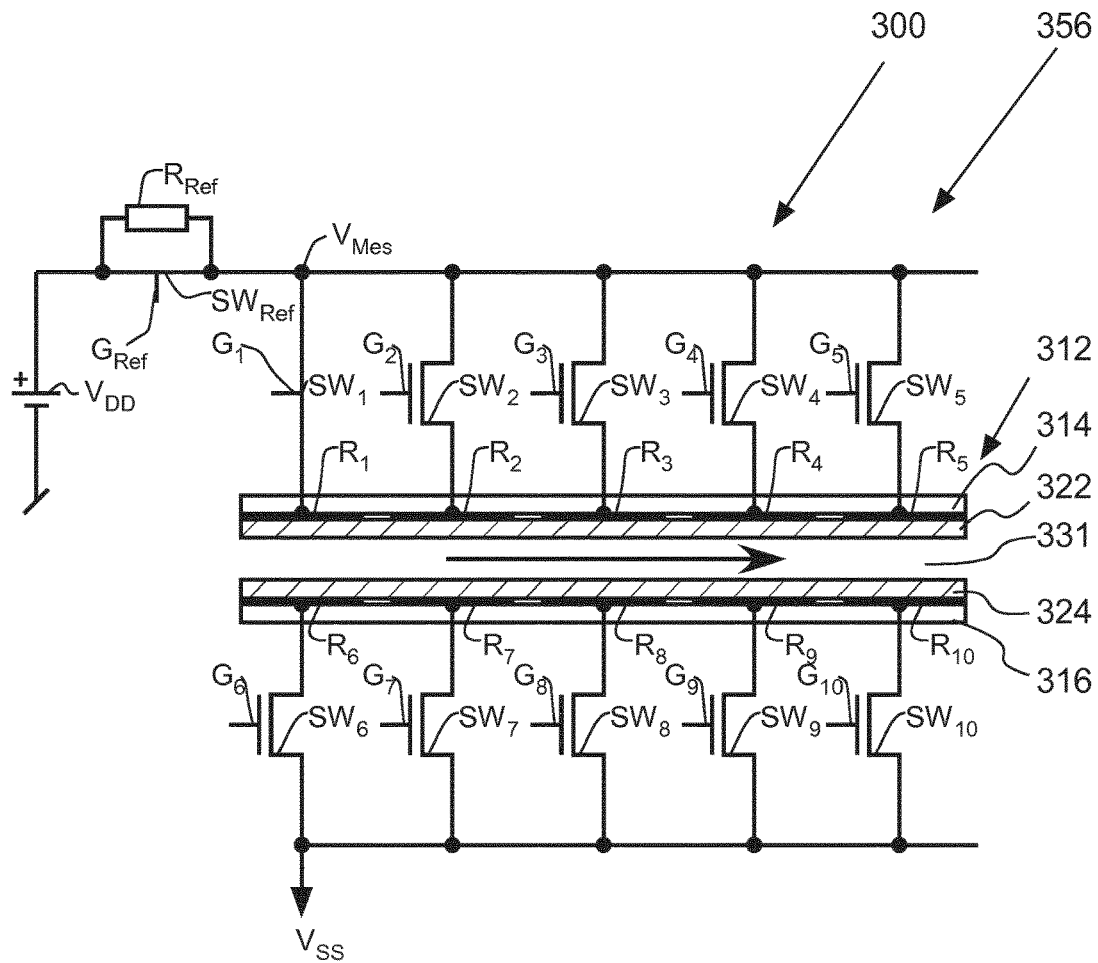
FIG. 7a shows the block diagram of the heating unit of FIG. 6 in heating mode.
Figure 7B:
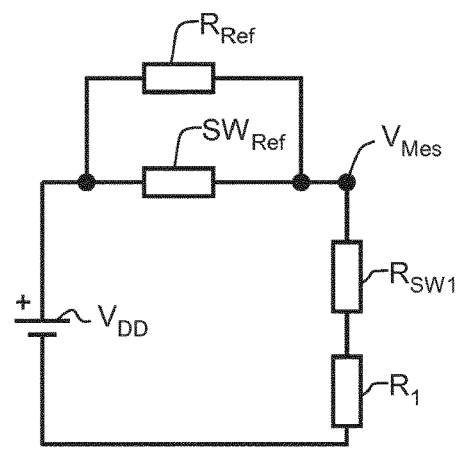
FIG. 7b shows a diagram of the electrical circuit in heating mode.

FIG. 7a shows the block diagram of the heating unit of FIG. 6 in heating mode and FIG. 7b shows an equivalent diagram of the electrical circuit 356 in heating mode.

In FIG. 7a the reference switch $G_{Ref}$ is closed and the switch $G_1/SW_1$ is closed. Therefore the first resistive pattern $R_1$ is coupled to the DC power supply input $V_{DD}$ during a first time period of operation.

In FIG. 7b the equivalent electrical circuit corresponding to the heating mode for the electrically resistive pattern $R_1$ is shown.

The reference resistor $R_{Ref}$ is coupled in parallel with the resistance $SW_{Ref}$ of the switch $G_{Ref}$. The resistance of the switch $SW_1$ and the electrically resistive pattern $R_1$ is coupled in series with the former two resistances. The electrically resistive pattern $R_1$ is connected to the negative side of the DC power supply voltage.

The resistance of the reference resistor $R_{Ref}$ is 75 ohm and the resistance of each of the switches $G_{Ref}$, $SW_1$ is approximately 15 mohm. The majority of the power delivered by the DC power supply $V_{DD}$ is dissipated in the electrically resistive pattern $R_1$. In an example the resistance of the electrically resistive pattern $R_1$ is 5 ohm. With a 24 VDC of the DC power supply $V_{DD}$ an electric power of 114 W will be dissipated in the electrically resistive pattern $R_1$.

Figure 8A:
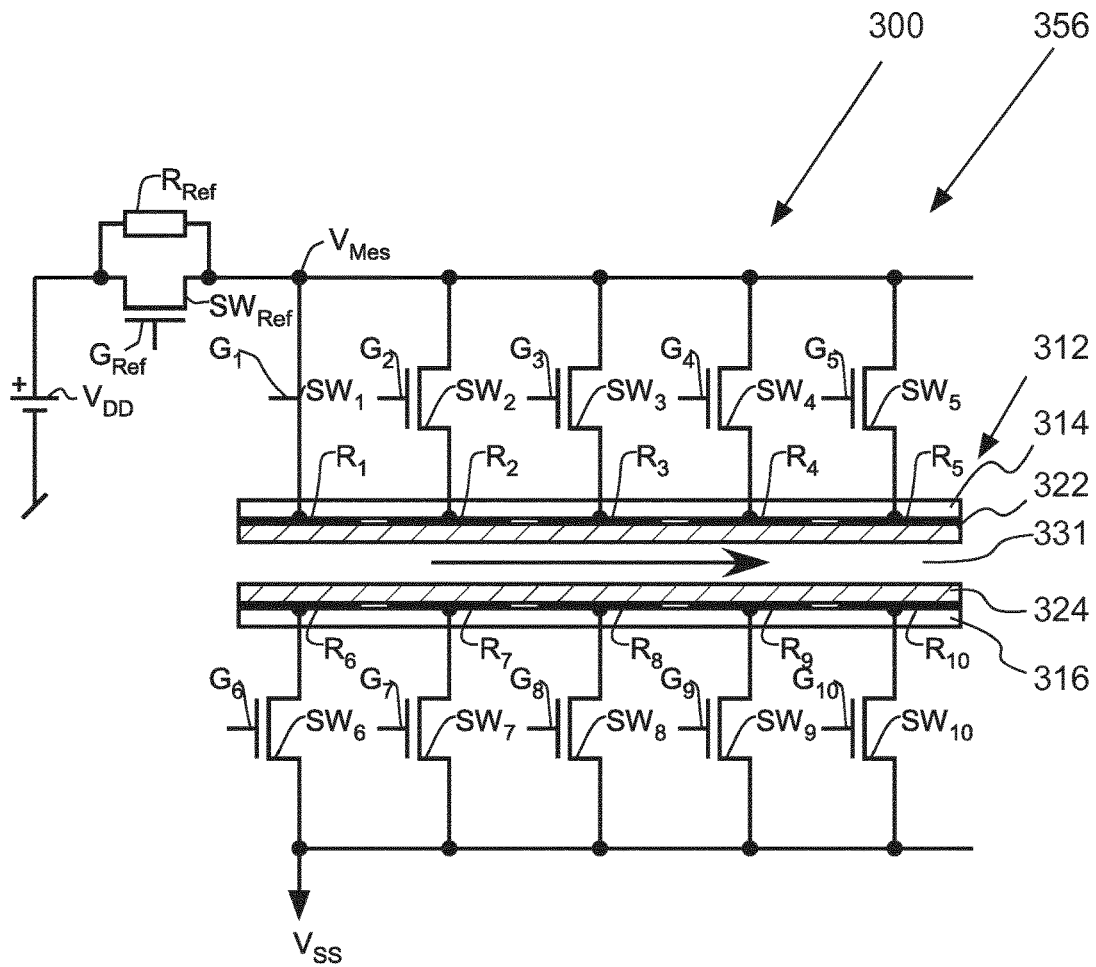
FIG. 8a shows the block diagram of the heating unit of FIG. 6 in temperature measuring mode.
Figure 8B:
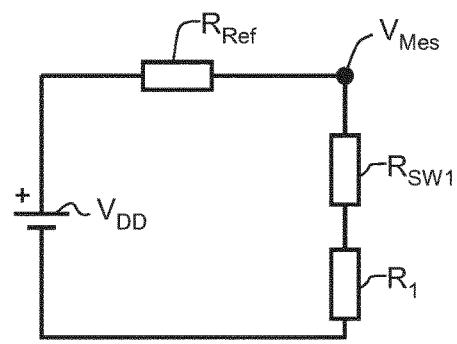
FIG. 8b shows a diagram of the electrical circuit in temperature measuring mode.

FIG. 8a shows the block diagram of the heating unit of FIG. 6 in temperature measuring mode during a second time period. FIG. 8b shows an equivalent diagram of the electrical circuit 356 in the temperature measuring mode.

In FIG. 8a the reference switch $G_{Ref}/SW_{Ref}$ is open or non-conducting and the switch $G_1/SW_1$ is closed or conducting. The reference resistor $R_{Ref}$ is coupled in series with the switch $G_1/SW_1$ and the electrically resistive pattern $R_1$. The electrically resistive pattern $R_1$ is connected to the negative side of the DC power supply input.

The DC voltage of the DC power supply $V_{DD}$ is known in advance or measured during operation of the heating unit 300 and voltage is measured at $V_{Mes}$.

Based on the measured DC voltage at $V_{Mes}$ and the known resistance of the reference resistor $R_{Ref}$ the current in the circuit can be calculated. As a resistance of $R_{SW1}$ is either known, or preferably insignificant compared to the resistance of $R_1$, the resistance of the electrically resistive pattern $R_1$ is the only unknown. Hence the resistance of $R_1$ can easily be determined or calculated based on the known circuit variables.

The determined resistance of the electrically resistive pattern $R_1$ allows the instantaneous temperature of the electrically resistive pattern $R_1$ to be determined or computed based on a known temperature coefficient of the electrically resistive pattern $R_1$. The instantaneous temperature of the electrically resistive pattern $R_1$ is used for controlling the heating.

Figure 9:
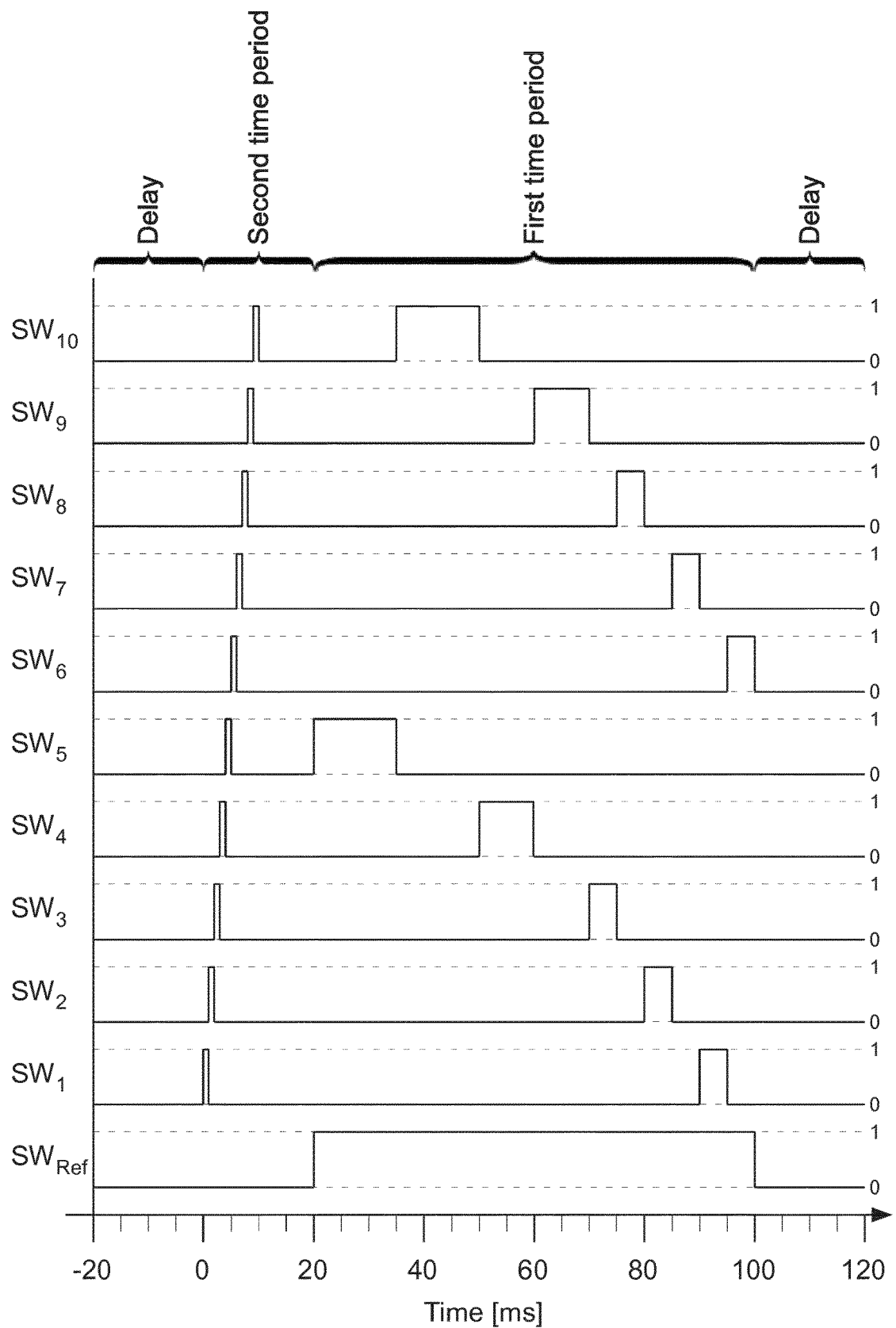
FIG. 9 shows a state/time diagram of the switches in the heating unit.

FIG. 9 shows a state/time diagram showing an example of the respective states, i.e. either conducting/closed or non-conducting/open, of the switches $SW_{Ref}$, $SW_1$, $SW_2$, $SW_3$, $SW_4$, $SW_5$, $SW_6$, $SW_7$, $SW_8$, $SW_9$, $SW_{10}$ of the heating unit of FIG. 6 during a time period of 140 ms.

In the diagram a value of 0 indicates that a switch is open and a value of 1 indicates that a switch is closed.

In the present exemplary embodiment, the first time period is set to last 100 ms. The first time period is subdivided into 5 ms ticks or sub-intervals defining a minimum time a switch can be closed. Alternatively, the length of the first time period and the subdivision can be adjusted to other lengths as required by a particular application, for example if the precision of the temperature control needs to be improved.

The second time period is set to last for 20 ms and is subdivided into 1 ms ticks. The controller may select to close or open a switch for a minimum duration of 1 ms. However, the measurements may be completed within a much smaller duration, i.e. as little as 1.5 ms for all resistors.

The diagram shows the three distinct time periods. From −20 ms to 0 ms-a delay where all switches are open. From 0 ms to 20 ms-a second time period, where the temperature of each electrically resistive pattern $R_1$, $R_2$, $R_3$, $R_4$, $R_5$, $R_6$, $R_7$, $R_8$, $R_9$, $R_{10}$ is determined. From 20 ms to 100 ms-a first time period where the DC power supply is selectively connected to the resistive patterns $R_1$, $R_2$, $R_3$, $R_4$, $R_5$, $R_6$, $R_7$, $R_8$, $R_9$, $R_{10}$. From 100 ms to 120 ms-a second delay period, where all switches are open.

During the delay periods, as previously mentioned, all switches are open. Therefore no power is dissipated in any of the electrically resistive patterns $R_1$, $R_2$, $R_3$, $R_4$, $R_5$, $R_6$, $R_7$, $R_8$, $R_9$, $R_{10}$. The temperature of said electrically resistive patterns $R_1$, $R_2$, $R_3$, $R_4$, $R_5$, $R_6$, $R_7$, $R_8$, $R_9$, $R_{10}$ will therefore converge towards the temperature of the infusion fluid in the fluid channel 331 or passage in the heat exchanger 312 due to the good thermal coupling between the infusion fluid in the fluid channel 331 or passage and the PCB holding the resistive patterns via the aluminium heat exchanger.

During the second time period each of the switches $SW_1$, $SW_2$, $SW_3$, $SW_4$, $SW_5$, $SW_6$, $SW_7$, $SW_8$, $SW_9$, $SW_{10}$ is closed briefly one after the other to sequentially connect the electrically resistive pattern $R_1$, $R_2$, $R_3$, $R_4$, $R_5$, $R_6$, $R_7$, $R_8$, $R_9$, $R_{10}$ to the DC power supply inlet for measuring the voltage at the junction point $V_{MES}$ and thereby determine the temperature of each electrically resistive pattern $R_1$, $R_2$, $R_3$, $R_4$, $R_5$, $R_6$, $R_7$, $R_8$, $R_9$, $R_{10}$. Each switch may be closed for a brief a time period as possible to limit the power dissipation in each resistive pattern.

The controller performs power management based on the temperature measurements. The controller 352 calculates the required power to be dissipated in order to maintain or increase the temperature of the infusion fluid in the fluid channel 331 or passage. The power dissipation may be distributed between the electrically resistive patterns $R_1$, $R_2$, $R_3$, $R_4$, $R_5$, $R_6$, $R_7$, $R_8$, $R_9$, $R_{10}$ such that the coldest resistive patterns are prioritised. Moreover, the maximum current that can be drawn from the DC power supply input may also be considered.

In the present example it is assumed that the temperature determination during the second time period has found that the temperature of the infusion fluid decreases towards the outlet end. Therefore, the resistive patterns and corresponding switches closer to the outlet is prioritised during the subsequent first time period initiated at 20 ms. Switch $SW_{Ref}$ is closed from 20 ms to 100 ms that is the complete duration of the first time period in order to connect the DC power supply input in heating mode. Switches $SW_5$ and $SW_{10}$ that lead to power dissipation in the resistive patterns closest to the outlet end are closed as the first switches for 15 ms each. Then switches $SW_4$ and $SW_9$ are closed for 10 ms. The remaining switches in the following order $SW_3$, $SW_8$, $SW_2$, $SW_7$, $SW_1$, and $SW_6$ are closed for 5 ms each. Therefore, more power has been dissipated in the electrically resistive patterns $R_4$, $R_5$, $R_9$, $R_{10}$ closer to the outlet than dissipated in the other electrically resistive patterns. Therefore, a higher temperature of the infusion fluid may be seen closer to the outlet end during the next temperature measurement after the second delay period (100 ms to 120 ms).

In subsequent first time periods the order and duration in which the switches open and close may change according to the temperature determination in the second time period immediately prior to a following first time period.

It is to be noted that the figures and the above description have shown the exemplary embodiments of the infusion fluid warmer in a simple and schematic manner.

The invention claimed is:

1. An infusion fluid warmer comprising:
   a DC power supply input,
   a first carrier board comprising a first surface and a second, opposing, surface, wherein the second surface comprises a first integrally formed electrically resistive pattern,
   a heat exchanger comprising an aluminium upper wall structure and a lower, opposing, wall structure separated by a fluid channel extending between fluid inlets and outlets of the heat exchanger; wherein the fluid channel extends substantially straight along a longitudinal axis of the heat exchanger; and
   a controller for connecting the DC power supply input to the first integrally formed electrically resistive pattern, wherein an outer surface of the upper wall structure is thermally connected to the first resistive pattern, and that the controller is configured to:
   connecting the DC power supply input to the first or second integrally formed electrically resistive pattern during a first time period to dissipate power in the first or second integrally formed electrically resistive pattern to thereby serve as a heating element during the first time period, wherein a width-to-thickness ratio of a central zone of the fluid channel is at least 50:1 or at least 175:1 or at least 350:1.

2. The infusion fluid warmer according to claim 1, wherein the controller is further configured to:
   disconnect the first integrally formed electrically resistive pattern from the DC power supply input during a predetermined delay time, determining, during a second time period, following the predetermined delay time, a resistance of the first integrally formed electrically resistive pattern,
   determining a temperature of the first integrally formed electrically resistive pattern based on the determined resistance.

3. The infusion fluid warmer according to claim 2, wherein the electronic switching circuit further comprises:
   a first controllable semiconductor switch coupled in series between the DC power supply input and the first integrally formed electrically resistive pattern and a first reference resistor connected across input and output terminals of the first controllable semiconductor switch.

4. The infusion fluid warmer according to claim 3, wherein a resistance of the first reference resistor is at least 100 times larger than an on-resistance of the first controllable semiconductor switch.

5. The infusion fluid warmer according to claim 1, wherein the controller is configured for selectively connecting and disconnecting the DC power supply input to the integrally formed electrically resistive pattern over time to control the temperature of the infusion fluid in accordance with a desired or target temperature of the infusion fluid.

6. The infusion fluid warmer according to claim 1, wherein the first carrier board comprises a printed circuit board (PCB).

7. The infusion fluid warmer according to claim 1, wherein each of the upper wall structure and the lower wall structure has a plate shaped structure with a thickness less than 5 mm, or less than 3 mm.

8. The infusion fluid warmer according to claim 1, wherein the fluid channel comprises a cavity formed in the upper wall structure.

9. The infusion fluid warmer according to claim 1, further comprising:
an outer housing or casing surrounding and enclosing at least the heat exchanger, the first carrier board and the second carrier board; and
an electrically insulating frame, gasket or ring surrounding and contacting peripheral edges of the upper and lower wall structures of the heat exchanger to prevent physical contact and electrical contact between the heat exchanger and the outer housing.

10. The infusion fluid warmer according to claim 9, wherein the fluid channel comprises an inlet transition zone at the fluid inlet, a central zone and an outlet transition zone at the fluid outlet; wherein the central zone has a rectangular cross-section in a longitudinal direction of the heat exchanger along a fluid flow path of the infusion fluid.

11. The infusion fluid warmer according to claim 1, wherein a thickness of the central zone of the fluid channel is between 0.1 mm and 0.5 mm.

12. The infusion fluid warmer according to claim 1, wherein a second surface of the first carrier board is plane and arranged to contact a complementary shaped plane surface of the aluminium upper wall structure; and the second surface of the second carrier board is plane and arranged to contact a complementary shaped plane surface of the lower wall structure.

13. The infusion fluid warmer according to claim 12, wherein the first integrally formed electrically resistive pattern and said at least one additional and separate integrally formed electrically resistive patterns are arranged sequentially along the second surface of the first carrier board.

14. The infusion fluid warmer according to claim 1, wherein a resistance of the first integrally formed electrically resistive pattern is less than 11Ω or between 1Ω and 7Ω.

15. The infusion fluid warmer according to claim 1, wherein each of the upper wall structure and lower wall structure is composed of a material having thermal conductivity equal to or exceeding 15 W/(m·K).

16. The infusion fluid warmer according to claim 1, wherein each of the upper wall structure and lower wall structure comprises at least one of thermally conductive polymer, aluminium, or stainless steel.

17. The infusion fluid warmer according to claim 16, wherein each of the upper wall structure and lower wall structures are composed of aluminium where the respective surfaces of the upper wall and lower wall structures are anodized by an aluminium oxide layer to provide a biocompatible layer in the fluid channel.

* * * * *